United States Patent
Shan et al.

(10) Patent No.: US 9,573,891 B2
(45) Date of Patent: Feb. 21, 2017

(54) COMPLEXES OF AGOMELATINE AND SULPHONIC ACIDS, A PROCESS FOR THEIR PREPARATION AND PHARMACEUTICAL COMPOSITIONS CONTAINING THEM

(71) Applicants: LES LABORATOIRES SERVIER, Suresnes (FR); SHANGHAI INSTITUTE OF PHARMACEUTICAL INDUSTRY, Jing'an District, Shanghai (CN)

(72) Inventors: Hanbin Shan, Gaoan (CN); Yuhui Shen, Shanghai (CN); Ying Luo, NanChang (CN); Philippe Letellier, Orléans (FR); Michael Lynch, Saint Jean de la Ruelle (FR)

(73) Assignees: LES LABORATOIRES SERVIER, Suresnes (FR); SHANGHAI INSTITUTE OF PHARMACEUTICAL INDUSTRY, Jing'an District, Shanghai (CN)

( * ) Notice: Subject to any disclaimer, the term of this patent is extended or adjusted under 35 U.S.C. 154(b) by 0 days.

(21) Appl. No.: 14/907,670

(22) PCT Filed: Jul. 28, 2014

(86) PCT No.: PCT/FR2014/051944
§ 371 (c)(1),
(2) Date: Jan. 26, 2016

(87) PCT Pub. No.: WO2015/015102
PCT Pub. Date: Feb. 5, 2015

(65) Prior Publication Data
US 2016/0159735 A1 Jun. 9, 2016

(30) Foreign Application Priority Data

Jul. 29, 2013 (WO) ................ PCT/CN2013/080337
Oct. 17, 2013 (FR) ...................... 13 60124

(51) Int. Cl.
*C07C 309/35* (2006.01)
*C07C 231/12* (2006.01)
*C07C 233/18* (2006.01)
*C07C 303/22* (2006.01)
*C07C 309/29* (2006.01)

(52) U.S. Cl.
CPC .......... *C07C 309/35* (2013.01); *C07C 231/12* (2013.01); *C07C 233/18* (2013.01); *C07C 303/22* (2013.01); *C07C 309/29* (2013.01)

(58) Field of Classification Search
CPC .... C07C 309/15; C07C 321/12; C07C 233/18; C07C 303/22; C07C 309/29
USPC ........................................................ 514/577
See application file for complete search history.

(56) References Cited

U.S. PATENT DOCUMENTS 9,409,857 B2 * 8/2016 Wang .................... C07C 233/18
2015/0141519 A1   5/2015 Wang

FOREIGN PATENT DOCUMENTS

EP        2517700       10/2012
WO    WO 2013/170738    11/2013

OTHER PUBLICATIONS

International Search Report for PCT/FR2014/051944 of Oct. 9, 2015.

* cited by examiner

*Primary Examiner* — Yevegeny Valenrod
(74) *Attorney, Agent, or Firm* — Hueschen and Sage

(57) ABSTRACT

Complexes of agomelatine and sulphonic acids of formula (I):

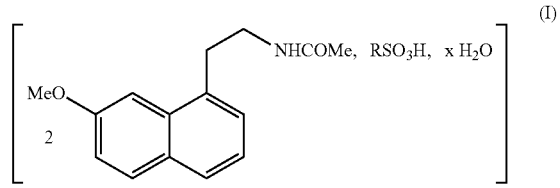

Medicinal products containing the same which are useful in treating disorders of the melatoninergic system.

14 Claims, 3 Drawing Sheets

COMPLEXES OF AGOMELATINE AND SULPHONIC ACIDS, A PROCESS FOR THEIR PREPARATION AND PHARMACEUTICAL COMPOSITIONS CONTAINING THEM

The present invention relates to new complexes of agomelatine and sulphonic acids, to a process for their preparation and also to pharmaceutical compositions containing them.

Agomelatine, or N-[2-(7-methoxy-1-naphthyl)ethyl]acetamide, has the structure of formula (II):

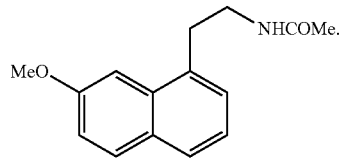

(II)

Agomelatine is marketed under the trade names Valdoxan® or Thymanax® by the French group Servier as an agonist of receptors of the melatoninergic system and an antagonist of the 5-$HT_{2C}$ receptor. It is the first antidepressant of the melatoninergic type, and is useful in the treatment of major depression, improving sleep and sexual function.

Agomelatine, its preparation and its therapeutic use have been described in the European Patent specifications EP 0 447 285 and EP 1 564 202.

The present invention relates to preparation of complexes of agomelatine and sulphonic acids which have the particular stoichiometry of 2 molar equivalents of agomelatine per 1 molar equivalent of sulphonic acids. These complexes have excellent properties in terms of solubility, stability and purity, making it possible to envisage their use in the manufacture of pharmaceutical compositions comprising agomelatine. Furthermore, the stoichiometry of the complexes according to the present invention provides an advantage in terms of the weight of the active component of the complex, i.e. the agomelatine, making it possible to prepare pharmaceutical formulations which contain lower amounts of the complex.

The present invention relates to complexes of agomelatine and sulphonic acids which have the structure of formula (I):

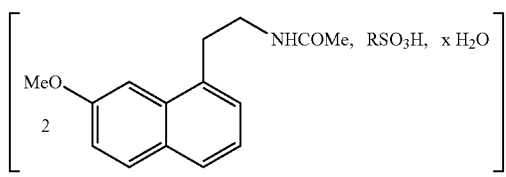

(I)

wherein x represents 0 or 1, and $RSO_3H$ represents 1,5-naphthalenedisulphonic acid or benzenesulphonic acid.

Preferred compounds according to the invention are the following complexes of agomelatine and sulphonic acids:
 agomelatine/1,5-naphthalenedisulphonic acid (2/1) complex,
 agomelatine/1,5-naphthalenedisulphonic acid (2/1) monohydrate complex,
 agomelatine/benzenesulphonic acid (2/1) complex.

Figure 1:
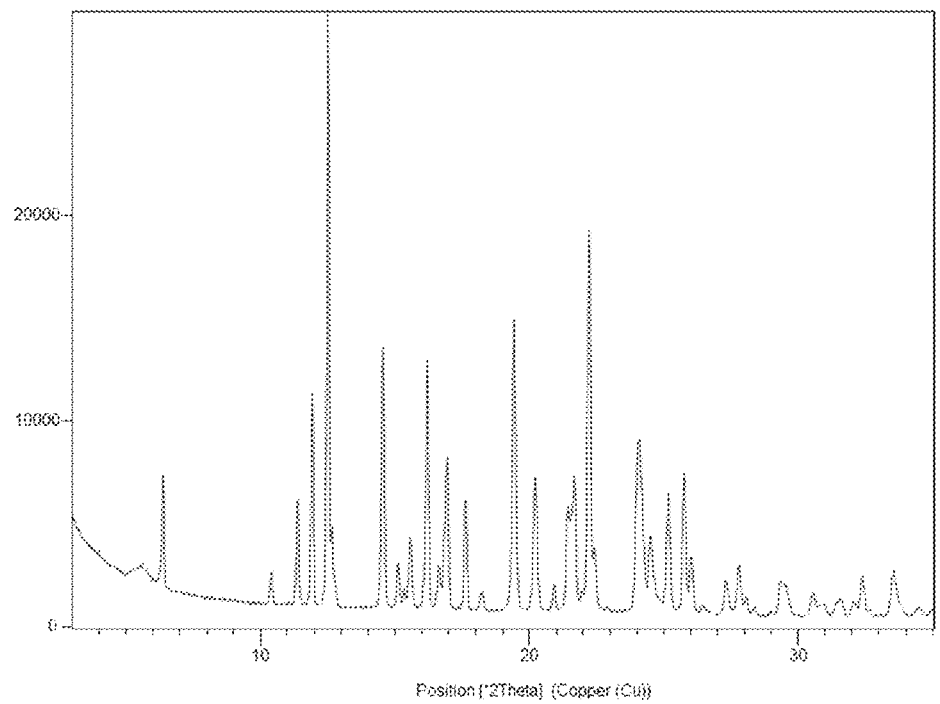

The agomelatine/1,5-naphthalenedisulphonic acid (2/1) complex is characterised by its X-ray powder diffraction diagram shown in FIG. 1, measured using a Panalytical Xpert Pro MPD diffractometer (copper anticathode). The principal lines are expressed in terms of interplanar distance d, Bragg's angle 2 theta (expressed in °±0.2), and relative intensity (expressed as a percentage relative to the most intense line) and are listed in Table 1:

TABLE 1

Table of the diffraction peaks of the agomelatine/1,5-naphthalenedisulphonic acid (2/1) complex

| 2-Theta (°) exp. | d (Å) exp. | Intensity (%) |
| --- | --- | --- |
| 6.3716 | 13.87229 | 18.97 |
| 11.3804 | 7.77552 | 17.98 |
| 11.9227 | 7.42299 | 36.06 |
| 12.5064 | 7.07784 | 100.00 |
| 12.6590 | 6.99288 | 13.75 |
| 14.5508 | 6.08767 | 44.17 |
| 15.5658 | 5.69292 | 11.96 |
| 16.2029 | 5.47051 | 42.63 |
| 16.9421 | 5.23346 | 25.85 |
| 17.6267 | 5.03171 | 18.67 |
| 19.4300 | 4.56857 | 49.04 |
| 20.2146 | 4.39301 | 22.77 |
| 21.4353 | 4.14550 | 17.80 |
| 21.6713 | 4.10090 | 22.84 |
| 22.2180 | 4.00121 | 64.19 |
| 22.4174 | 3.96607 | 10.83 |
| 24.0749 | 3.69664 | 29.61 |
| 24.5048 | 3.63275 | 13.33 |
| 25.1744 | 3.53763 | 20.58 |
| 25.7599 | 3.45853 | 23.59 |

When the complex of the present invention is characterised by X-ray diffraction measurement, there may be errors of measurement of the identified peaks which are sometimes attributable to the equipment or to the conditions used. More especially, the 2 theta values can have an error of approximately ±0.2 and sometimes an error of approximately ±0.1, even if sophisticated equipment is used. The measurement error must accordingly be taken into account when identifying the structure of the complex.

The crystalline structure of the agomelatine/1,5-naphthalenedisulphonic acid (2/1) complex was determined and the following parameters were identified:

Space group: P 1 21/c 1 (14)

Lattice parameters: a=8.4970(3)Å, b=8.0873(3)Å, c=27.7107(9)Å; α=90°, β=93.059(2)°, γ=90°

Volume of unit cell: $V_{unit\ cell}$=1901.51100 Å$^3$

Figure 2:
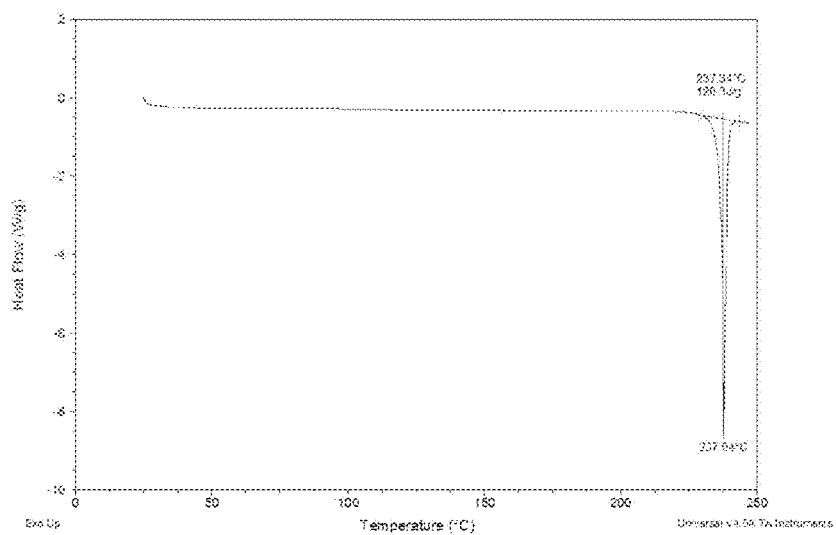

The agomelatine/1,5-naphthalenedisulphonic acid (2/1) complex is also characterised by DSC (differential scanning calorimetry) in the spectrum shown in FIG. 2, which shows an endotherm corresponding to melting of the complex at a temperature of approximately 237° C.

Figure 3:
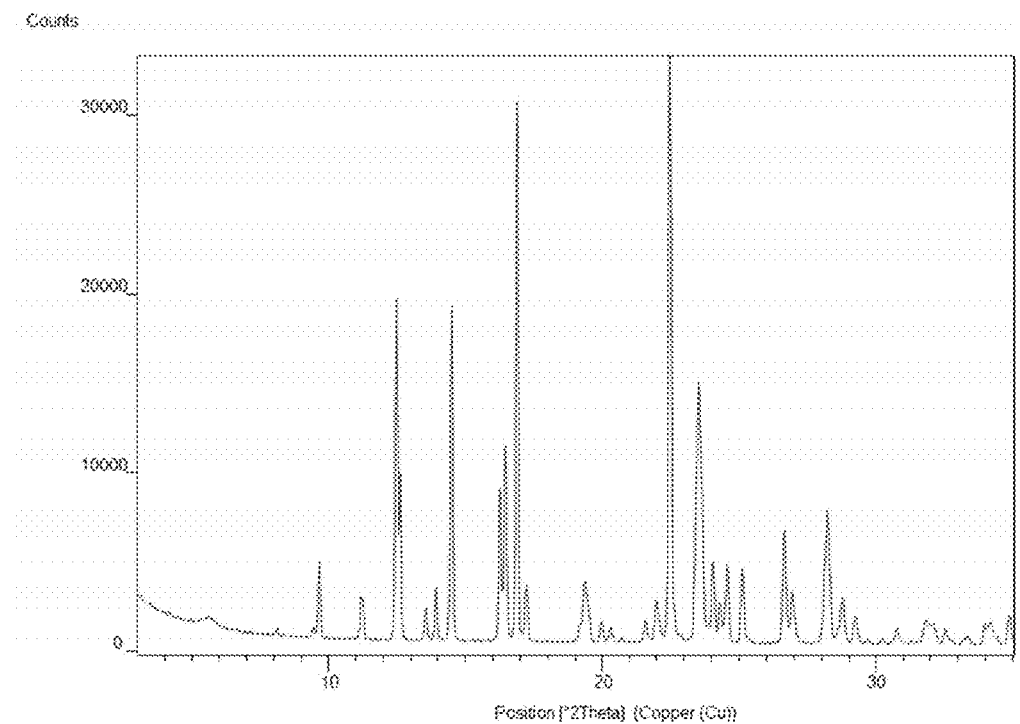

The invention relates also to the agomelatine/1,5-naphthalenedisulphonic acid (2/1) monohydrate complex which is characterised by its X-ray powder diffraction diagram shown in FIG. 3, measured using a Panalytical Xpert Pro MPD diffractometer (copper anticathode). The principal lines are expressed in terms of interplanar distance d, Bragg's angle 2 theta (expressed in °±0.2), and relative intensity (expressed as a percentage relative to the most intense line) and are listed in Table 2:

TABLE 2

Table of the diffraction peaks of the agomelatine/1,5-naphthalenedisulphonic acid (2/1) monohydrate complex

| 2-Theta (°) exp. | d (Å) exp. | Intensity (%) |
|---|---|---|
| 9.6680 | 9.14852 | 12.45 |
| 12.4885 | 7.08796 | 57.23 |
| 12.6164 | 7.01639 | 28.61 |
| 14.5042 | 6.10715 | 57.42 |
| 16.2684 | 5.44863 | 25.67 |
| 16.4624 | 5.38484 | 32.93 |
| 16.8967 | 5.24739 | 90.90 |
| 19.3772 | 4.58091 | 10.50 |
| 22.4767 | 3.95573 | 100.00 |
| 23.4111 | 3.79992 | 20.49 |
| 23.5330 | 3.78051 | 44.02 |
| 23.6735 | 3.75840 | 21.92 |
| 24.0477 | 3.70076 | 13.67 |
| 24.5716 | 3.62303 | 13.43 |
| 25.1240 | 3.54460 | 12.46 |
| 26.6602 | 3.34374 | 19.10 |
| 28.1333 | 3.16930 | 12.07 |
| 28.2443 | 3.15971 | 22.49 |

When the complex of the present invention is characterised by X-ray diffraction measurement, there may be errors of measurement of the identified peaks which are sometimes attributable to the equipment or to the conditions used. More especially, the 2 theta values can have an error of approximately ±0.2 and sometimes an error of approximately ±0.1, even if sophisticated equipment is used. The measurement error must accordingly be taken into account when identifying the structure of the complex.

The crystalline structure of the agomelatine/1,5-naphthalenedisulphonic acid (2/1) monohydrate complex was determined and the following parameters were identified:

Space group: P-1 (2)
Lattice parameters: a=9.5673(3)Å, b=9.7223(3)Å, c=11.4632(3)Å; α=76.967(2)°, β=75.339(1)°, γ=78.675(2)°
Volume of unit cell: $V_{unit\ cell}$=993.93800 Å$^3$ The agomelatine/1,5-naphthalenedisulphonic acid (2/1) monohydrate complex is also characterised by DSC (differential scanning calorimetry) in the spectrum shown in FIG. 4, which shows two endotherms: one at approximately 116° C., corresponding to dehydration of the complex, and the other at approximately 238° C., corresponding to melting of the complex.

Figure 5:
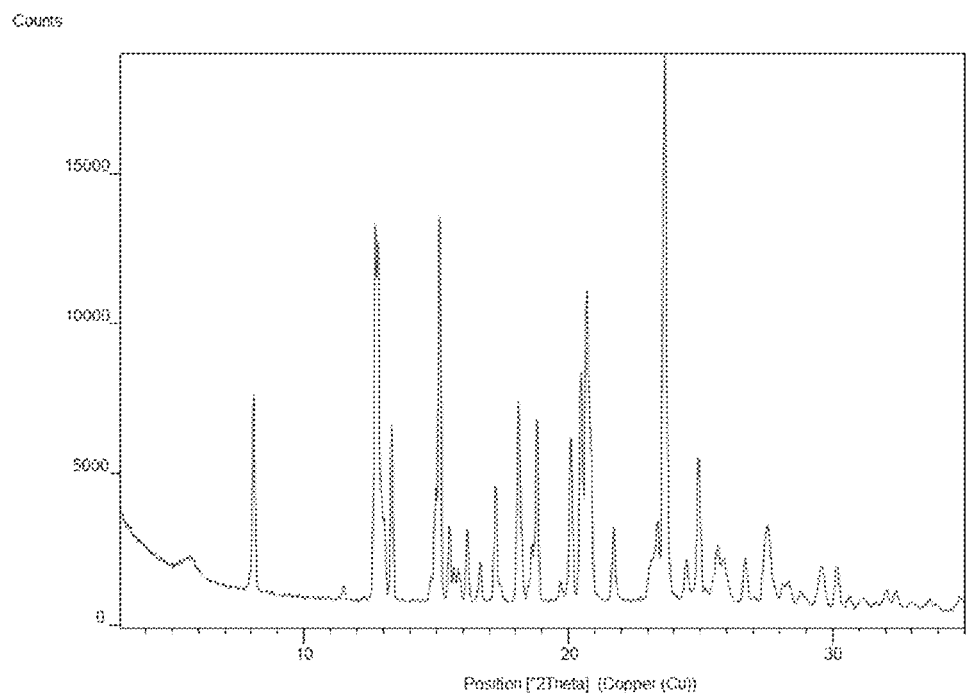

The invention relates also to the agomelatine/benzenesulphonic acid (2/1) complex which is characterised by its X-ray powder diffraction diagram shown in FIG. 5, measured using a Panalytical Xpert Pro MPD diffractometer (copper anticathode). The principal lines are expressed in terms of interplanar distance d, Bragg's angle 2 theta (expressed in °±0.2), and relative intensity (expressed as a percentage relative to the most intense line) and are listed in Table 3:

TABLE 3

Table of the diffraction peaks of the agomelatine/benzenesulphonic acid (2/1) complex

| 2-Theta (°) exp. | d (Å) exp. | Intensity (%) |
|---|---|---|
| 8.0711 | 10.95469 | 35.25 |
| 12.6820 | 6.98026 | 68.37 |
| 12.7706 | 6.93203 | 65.37 |
| 13.0114 | 6.80427 | 15.18 |
| 13.3054 | 6.65458 | 31.84 |
| 14.9475 | 5.92700 | 19.42 |
| 15.1121 | 5.86283 | 70.19 |
| 15.4873 | 5.72160 | 14.16 |
| 16.1644 | 5.48344 | 12.98 |
| 17.2360 | 5.14486 | 21.06 |
| 18.1046 | 4.89993 | 36.33 |
| 18.6255 | 4.76406 | 10.91 |
| 18.8009 | 4.72001 | 33.43 |
| 20.0908 | 4.41978 | 30.26 |
| 20.4742 | 4.33788 | 42.37 |
| 20.6921 | 4.29270 | 56.78 |
| 20.8640 | 4.25771 | 26.42 |
| 21.7142 | 4.09289 | 13.88 |
| 23.3683 | 3.80679 | 15.16 |
| 23.6410 | 3.76349 | 100.00 |
| 24.9314 | 3.57154 | 26.81 |
| 25.6543 | 3.47253 | 10.71 |
| 27.5599 | 3.23660 | 14.00 |

When the complex of the present invention is characterised by X-ray diffraction measurement, there may be errors of measurement of the identified peaks which are sometimes attributable to the equipment or to the conditions used. More especially, the 2 theta values can have an error of approximately ±0.2 and sometimes an error of approximately ±0.1, even if sophisticated equipment is used. The measurement error must accordingly be taken into account when identifying the structure of the complex.

The crystalline structure of the agomelatine/benzenesulphonic acid (2/1) complex was determined and the following parameters were identified:

Space group: P-1 (2)
Lattice parameters: a=15.5878(8)Å, b=15.7088(6)Å, c=7.2091(3)Å; α=100.445(2)°, β=99.470(2)°, γ=89.054(3)°
Volume of unit cell: $V_{unit\ cell}$=1712.18900 Å

Figure 6:
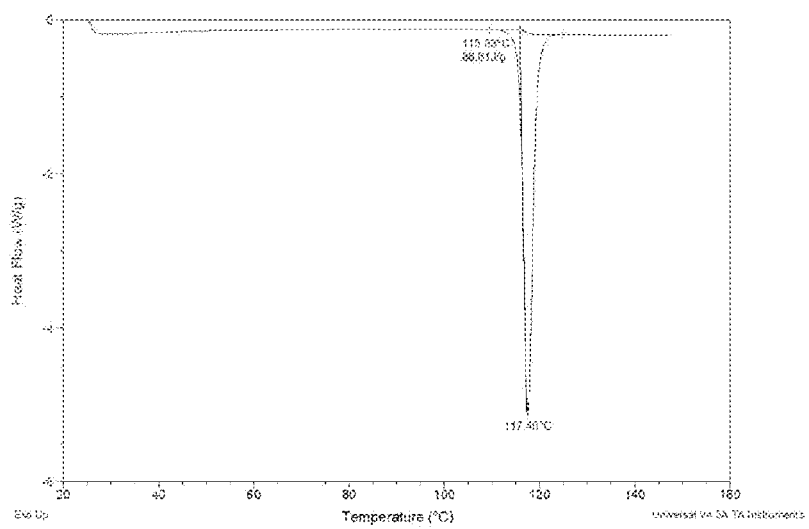

The agomelatine/benzenesulphonic acid (2/1) complex is also characterised by DSC (differential scanning calorimetry) in the spectrum shown in FIG. 6, which shows an endotherm at approximately 116° C., corresponding to melting of the complex.

The invention relates also to a process for obtaining complexes of agomelatine and sulphonic acids, wherein:
the two constituents are mixed in an organic or aqueous-organic solvent in the desired proportions;
the solution obtained is stirred and optionally heated at a temperature not greater than the boiling point of the chosen solvent;
the mixture is cooled, with stirring, and the complex precipitates naturally or precipitates after being taken up in a second solvent;
the precipitate obtained is filtered off and dried.

In the process according to the invention, the solvent used is preferably a ketone such as, for example, acetone; an ether such as, for example, diisopropyl ether, tetrahydrofuran or methyl tert-butyl ether; or an aromatic hydrocarbon such as, for example, toluene. When a second solvent is used in order to promote precipitation of the complex, the solvent chosen is an alcohol such as, for example, methanol, ethanol or tert-butanol; an alkane such as, for example, n-hexane or n-heptane; or benzonitrile.

An alternative process comprises co-grinding the two constituents of the co-crystal. The co-grinding is preferably carried out in a steel jar. A variant of this process comprises adding an organic solvent during the grinding; in this case, the co-crystal obtained is then dried. Among the solvents used, there may be mentioned, more especially, ketones such as, for example, acetone; or ethers such as, for example, diisopropyl ether or methyl tert-butyl ether. Alcohols such as, for example, methanol, ethanol or tert-butanol can also be used.

The grinding is advantageously carried out using non-oxidisable balls. The grinding is carried out using vibrations, preferably vibrations with a frequency ranging from 20 to 30 Hz. The vibrations are applied for a period which may range from 5 minutes to 3 hours.

Another alternative process comprises mixing two solutions containing each of the constituents and rapidly freezing the mixture obtained at very low temperature, and then at that same low temperature drying the co-crystal thereby obtained. The two constituents are advantageously mixed in an organic or aqueous-organic solvent. The freezing and drying are carried out preferably between −40° C. and −60° C., and more preferably at −40° C.

Another advantageous process according to the invention comprises mixing the powders of agomelatine and of the acid in question in a mixer and then extruding the mixture by twin-screw extrusion without a die in order to obtain a solid grain directly at the outlet of the extruder. The screw profile used is preferably a high-shear profile, optionally with the use of kneader elements allowing the contact surface between the constituents to be improved. The L/D parameter of the screw may vary between 10 and 40 and the speed of rotation between 10 and 200 rpm. The temperature used varies from 40 to 100° C.

The complexes of agomelatine and sulphonic acids that are obtained have a solubility that is increased very significantly relative to agomelatine per se, which renders them more suitable for the preparation of pharmaceutical formulations. The complexes of agomelatine and sulphonic acids according to the invention additionally exhibit excellent stability and very good purity. They are, moreover, obtained by a simple process which does not include any difficult steps.

The pharmaceutical forms comprising the complexes according to the invention will be used in the treatment of disorders of the melatoninergic system and, more especially, in the treatment of stress, sleep disorders, anxiety disorders and especially generalised anxiety disorder, obsessive compulsive disorders, mood disorders and especially bipolar disorders, major depression, seasonal affective disorder, cardiovascular pathologies, pathologies of the digestive system, insomnia and fatigue due to jet-lag, schizophrenia, panic attacks, melancholia, appetite disorders, obesity, insomnia, pain, psychotic disorders, epilepsy, diabetes, Parkinson's disease, senile dementia, various disorders associated with normal or pathological ageing, migraine, memory loss, Alzheimer's disease, and also in cerebral circulation disorders. In another field of activity, it will be possible to use the co-crystals according to the invention in sexual dysfunctions, as ovulation inhibitors and immunomodulators and in the treatment of cancers.

The invention relates also to pharmaceutical compositions comprising as active ingredient a complex of agomelatine and sulphonic acids according to the invention together with one or more adjuvants or excipients.

Among the pharmaceutical compositions according to the invention there may be mentioned, more especially, those that are suitable for oral, parenteral (intravenous or subcutaneous) or nasal administration, tablets or dragées, granules, sublingual tablets, capsules, lozenges, suppositories, creams, ointments, dermal gels, injectable preparations, drinkable suspensions and chewing gums.

The useful dosage can be varied according to the nature and severity of the disorder, the administration route and the age and weight of the patient. The dosage varies from 0.1 mg to 1 g of agomelatine per day in one or more administrations.

Representative examples of the present invention are illustrated with the corresponding Figures in order better to evaluate the subject-matter, features and advantages thereof.

FIG. 1: X-ray powder diffraction diagram of the agomelatine/1,5-naphthalene-disulphonic acid (2/1) complex of Example 1.

FIG. 2: DSC thermogram of the agomelatine/1,5-naphthalenedisulphonic acid (2/1) complex of Example 1.

FIG. 3: X-ray powder diffraction diagram of the agomelatine/1,5-naphthalene-disulphonic acid (2/1) monohydrate complex of Example 2.

Figure 4:
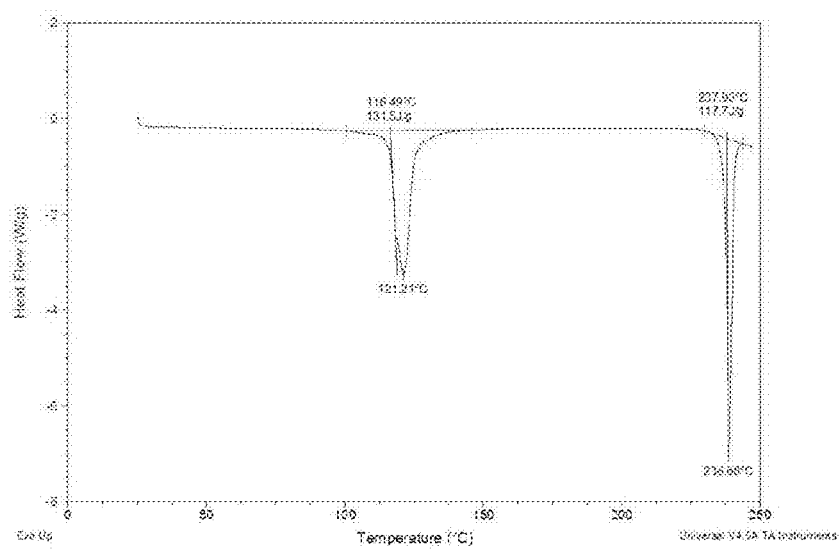

FIG. 4: DSC thermogram of the agomelatine/1,5-naphthalenedisulphonic acid (2/1) monohydrate complex of Example 2.

FIG. 5: X-ray powder diffraction diagram of the agomelatine/benzenesulphonic acid (2/1) complex of Example 3.

FIG. 6: DSC thermogram of the agomelatine/benzenesulphonic acid (2/1) complex of Example 3.

EXAMPLE 1

Agomelatine/1,5-Naphthalenedisulphonic Acid (2/1) Complex

Procedure 1

Agomelatine (5.00 g, 2 eq.) and anhydrous 1,5-naphthalenedisulphonic acid (2.96 g, 1 eq.) are placed in a reactor. 20 ml of acetone are added. The suspension is stirred under reflux for 1 hour and then immediately filtered. The cake is washed twice with acetone and then dried for 1 hour. 25 g of a white solid corresponding to the title product are obtained.

Yield: 78.5%

Melting point: 237° C.

Procedure 2

Agomelatine (2.98 g, 2 eq.) and 1,5-naphthalenedisulphonic acid tetrahydrate (2.18 g, 1 eq.) are transferred into a 250-ml flask. 100 ml of acetone are added and the reaction mixture is refluxed for 3 hours (crystallisation occurs after about 1 hour). The suspension is cooled to ambient temperature and stirred for 1 hour. 4.03 g of a white solid corresponding to the title product are isolated by filtration and are dried in vacuo (10 mbar) at 40° C. for 15 hours.

Yield: 85.0%

Melting point: 237° C.

Procedure 3

Agomelatine (5.00 g, 2 eq.) and anhydrous 1,5-naphthalenedisulphonic acid (2.96 g, 1 eq.) are placed in a reactor. 40 ml of methyl tert-butyl ether are added. The suspension is stirred under reflux for 3 hours and then immediately filtered. The cake is washed twice with methyl tert-butyl ether and then dried for 1 hour. 5.28 g of a white solid corresponding to the title product are obtained.

Yield: 66.3%

Melting point: 237° C.

EXAMPLE 2

Agomelatine/1,5-Naphthalenedisulphonic Acid (2/1) Monohydrate Complex

Procedure 1

Agomelatine (5.00 g, 1 eq.) and anhydrous 1,5-naphthalenedisulphonic acid (5.92 g, 1 eq.) are placed in a reactor. 10 ml of ethanol and 20 ml of water are added. The suspension is stirred under reflux for 0.5 hour so that it becomes clear. The mixture is then cooled naturally, with stirring, for 0.5 hour, and the suspension is filtered. The cake is washed with ethanol and water, and then dried for 1 hour. 5.15 g of a white solid are obtained.

Yield: 63.2%

Melting point: 116° C. (dehydration endotherm), 238° C.

Procedure 2

Agomelatine (5.00 g, 1 eq.) and 1,5-naphthalenedisulphonic acid tetrahydrate (7.40 g, 1 eq.) are transferred into a reactor. 10 ml of ethanol and 20 ml of water are added. The suspension is stirred under reflux for 0.5 hour so that it becomes clear. The mixture is then cooled naturally, with stirring, for 0.5 hour, and the suspension is filtered. The cake is washed with ethanol and water, and then dried for 1 hour. 4.90 g of a white solid are obtained.

Yield: 60.2%

Melting point: 116° C. (dehydration endotherm), 238° C.

Procedure 3

Agomelatine (0.5 g) and 1,5-naphthalenedisulphonic acid tetrahydrate (0.370 g) are placed in a 50-ml non-oxidisable jar. Two stainless steel balls of 12 mm diameter are added and the jar is closed. Vibrations with a frequency of 30 Hz are applied for 15 minutes to yield, after drying overnight at ambient temperature, 0.805 g of solid.

Melting point: 116° C. (dehydration endotherm), 238° C.

Procedure 4

Agomelatine (0.5 g) and 1,5-naphthalenedisulphonic acid tetrahydrate (0.370 g) are placed in a 50-ml non-oxidisable jar. Two stainless steel balls of 12 mm diameter are added and the jar is closed. 100 µl of methyl tert-butyl ether are added. Vibrations with a frequency of 30 Hz are applied for 30 minutes to yield, after drying overnight at ambient temperature, 0.803 g of solid.

Melting point: 116° C. (dehydration endotherm), 238° C.

EXAMPLE 3

Agomelatine/Benzenesulphonic Acid (2/1) Complex

Agomelatine (5.00 g, 2 eq.) and benzenesulphonic acid (1.62 g, 1 eq.) are transferred into a reactor. 10 ml of ethanol and 15 ml (10 ml+5 ml) of toluene are added. The suspension is stirred under reflux for 0.5 hour so that it becomes clear (if the solution is not clear, more ethanol is added until it does become clear). The mixture is then cooled naturally to 5° C., with stirring, for 0.5 hour, and the suspension is filtered. The cake is dried for 1 hour. 4.31 g of a white solid corresponding to the title product are obtained.

Yield: 65.2%

Melting point: 116° C.

In the examples above it is possible to use commercially available agomelatine or agomelatine prepared by one of the methods described in the prior art.

EXAMPLE 4

Pharmaceutical Compositions: Capsules Containing a Dose of 25 mg of Agomelatine Pharmaceutical Composition Containing the Compound of Example 1

| Formulation for the preparation of 1000 capsules each containing 25 mg of agomelatine | |
|---|---|
| Compound of Example 1 | 39.8 g |
| Lactose (Spherolac 100) | 85.2 g |
| Starch 1500 | 25.5 g |
| CMS-Na | 8.5 g |
| Ac-Di-Sol ® (FMC) | 17 g |
| Stearic acid | 3.4 g |

Pharmaceutical Composition Containing the Compound of Example 2

| Formulation for the preparation of 1000 capsules each containing 25 mg of agomelatine | |
|---|---|
| Compound of Example 2 | 40.7 g |
| Lactose (Spherolac 100) | 85.2 g |
| Starch 1500 | 25.5 g |
| CMS-Na | 8.5 g |
| Ac-Di-Sol ® (FMC) | 17 g |
| Stearic acid | 3.4 g |

Pharmaceutical Composition Containing the Compound of Example 3

| Formulation for the preparation of 1000 capsules each containing 25 mg of agomelatine | |
|---|---|
| Compound of Example 3 | 33.1 g |
| Lactose (Spherolac 100) | 85.2 g |
| Starch 1500 | 25.5 g |
| CMS-Na | 8.5 g |
| Ac-Di-Sol ® (FMC) | 17 g |
| Stearic acid | 3.4 g |

EXAMPLE 5

Pharmaceutical Compositions: Tablets Each Containing a Dose of 25 mg of Agomelatine Formulation for the Preparation of 1000 Tablets Each Containing 25 mg of Agomelatine:

| | |
|---|---|
| Compound of Example 1 | 39.8 g |
| Lactose monohydrate | 115 g |
| Magnesium stearate | 2 g |
| Maize starch | 33 g |
| Maltodextrins | 15 g |
| Anhydrous colloidal silica | 1 g |
| Pregelatinised maize starch, Type A | 9 g |

Formulation for the Preparation of 1000 Tablets Each Containing 25 mg of Agomelatine:

| | |
|---|---|
| Compound of Example 2 | 40.7 g |
| Lactose monohydrate | 115 g |

-continued

|  |  |
|---|---|
| Magnesium stearate | 2 g |
| Maize starch | 33 g |
| Maltodextrins | 15 g |
| Anhydrous colloidal silica | 1 g |
| Pregelatinised maize starch, Type A | 9 g |

Formulation for the Preparation of 1000 Tablets Each Containing 25 mg of Agomelatine:

|  |  |
|---|---|
| Compound of Example 3 | 33.1 g |
| Lactose monohydrate | 115 g |
| Magnesium stearate | 2 g |
| Maize starch | 33 g |
| Maltodextrins | 15 g |
| Anhydrous colloidal silica | 1 g |
| Pregelatinised maize starch, Type A | 9 g |

Detection Methods and Results

1. Purity of the Samples

Chromatography conditions: C18 column; mobile phase: phosphate buffer 10 mmol/L (adjusted to pH 7.0 with NaOH): acetonitrile 2:7 (v/v); temperature of the column: 40° C.; detection wavelength: 220 nm; internal standard method used with the compound of Example 1.

1 mg/ml solutions of the compounds of the invention are prepared with the mobile phase. 10 μl of each solution are injected into the liquid chromatography system and the chromatograms are recorded.

The compounds of the invention all have purities greater than or equal to 99%.

2. Stability

Samples of the compounds of Examples 1, 2 and 3 are placed in incubators under denaturing conditions and the stability is determined by DSC measurements over 2 months. The results are presented in Table 4:

TABLE 4

|  | 25° C., 60% RH OB | 50° C. CB | 70° C. CB |
|---|---|---|---|
| Compound of Example 1 | stable | stable | stable |
| Compound of Example 2 | stable | stable | stable |
| Compound of Example 3 | stable | stable | stable |

RH = relative humidity;
OB = open bottle;
CB = closed bottle

The compounds of the invention are stable under highly denaturing conditions, which is favourable for their use in pharmaceutical compositions.

3. Solubility

Using an external standard method, the compounds of Examples 1, 2 and 3 are tested by HPLC and compared with agomelatine of form II. The results are presented in Table 5 in the form of % increase in solubility relative to the solubility of agomelatine of form II:

TABLE 5

|  | Solubility (increase versus agomelatine form II) | | |
|---|---|---|---|
| Sample | in water | in 0.1N HCl | in a buffer pH 6.8 |
| Compound of Example 1 | +18% | +25% | +48% |
| Compound of Example 2 | +12% | +75% | +57% |
| Compound of Example 3 | +22% | +32% | +46% |

The results show that the complexes of agomelatine and sulphonic acids of the present invention have greater solubility than agomelatine of form II per se in water, in 0.1N HCl, which is similar to human gastric fluids, or in a buffer at pH 6.8. These results show that the complexes have a far better potential in terms of bioavailability than agomelatine of form II.

4. DSC Analyses

Approximately 5-10 mg of the compounds of Examples 1, 2 and 3 are weighed into an aluminium crucible closed with a pierced (non-hermetic) aluminium lid, unless specified otherwise. The sample is introduced into a TA Q1000 device (equipped with a cooler), cooled and maintained at 25° C. After thermal stabilisation, the sample and the reference are heated from 200° C. to 250° C. at a rate of 10° C./min and the response to the heat flow is recorded. Nitrogen is used as the purge gas, at a flow rate of 100 cm³/min.

The DSC thermograms obtained with the compounds of Examples 1, 2 and 3 are shown in FIGS. 2, 4 and 6.

5. Analysis of the Crystalline Structure

The conditions of measurement of the X-ray powder diffraction diagrams of the products of Examples 1, 2 and 3 are as follows:

Approximately 50 mg of the compounds of Examples 1, 2 and 3 are placed between two Kapton® films and fixed to the sample support. The sample is then placed in a PANALYTICAL XPERT-PRO MPD diffractometer in transmission mode under the following conditions:

Parameters of the generator: 45 kV/40 mA
Configuration theta/theta
Anode: Cu
K-Alpha1 [Å] 1.54060
K-Alpha2 [Å] 1.54443
K-Beta [Å] 1.39225
K-A2/K-A1 Ratio 0.50000
Scanning mode: continuous from 3° to 55° (Bragg's angle 2 theta)
Step [°2Th.] 0.0170
Step duration [s] 35.5301
Starting angle [°2Th.] 3.0034
Finishing angle [°2Th.] 54.9894
Rotation: yes The X-ray powder diffraction diagrams obtained for Examples 1, 2 and 3 are shown in FIGS. 1, 3 and 5.

The invention claimed is:

1. A complex of agomelatine and sulphonic acids of formula (I):

wherein x represents 0 or 1, and RSO₃H represents 1,5-naphthalenedisulphonic acid or benzenesulphonic acid.

2. The agomelatine complex according to claim 1, which is the agomelatine/1,5-naphthlenedisulphonic acid (2/1) complex.

3. The agomelatine complex according to claim 2, having the following X-ray powder diffraction diagram expressed in terms of interplanar distance d, Bragg's angle 2 theta (expressed in °±0.2), and relative intensity:

| 2-Theta (°) exp. | d (Å) exp. | Intensity (%) |
|---|---|---|
| 6.3716 | 13.87229 | 18.97 |
| 11.3804 | 7.77552 | 17.98 |
| 11.9227 | 7.42299 | 36.06 |
| 12.5064 | 7.07784 | 100.00 |
| 12.6590 | 6.99288 | 13.75 |
| 14.5508 | 6.08767 | 44.17 |
| 15.5658 | 5.69292 | 11.96 |
| 16.2029 | 5.47051 | 42.63 |
| 16.9421 | 5.23346 | 25.85 |
| 17.6267 | 5.03171 | 18.67 |
| 19.4300 | 4.56857 | 49.04 |
| 20.2146 | 4.39301 | 22.77 |
| 21.4353 | 4.14550 | 17.80 |
| 21.6713 | 4.10090 | 22.84 |
| 22.2180 | 4.00121 | 64.19 |
| 22.4174 | 3.96607 | 10.83 |
| 24.0749 | 3.69664 | 29.61 |
| 24.5048 | 3.63275 | 13.33 |
| 25.1744 | 3.53763 | 20.58 |
| 25.7599 | 3.45853 | 23.59 | including the forms whose diffraction angles correspond to within ±0.2°.

4. The agomelatine complex according to claim 1, which is the agomelatine/1,5-naphthlenedisulphonic acid (2/1) monohydrate complex.

5. The agomelatine complex according to claim 4, having the following X-ray powder diffraction diagram expressed in terms of interplanar distance d, Bragg's angle 2 theta (expressed in °±0.2), and relative intensity:

| 2-Theta (°) exp. | d (Å) exp. | Intensity (%) |
|---|---|---|
| 9.6680 | 9.14852 | 12.45 |
| 12.4885 | 7.08796 | 57.23 |
| 12.6164 | 7.01639 | 28.61 |
| 14.5042 | 6.10715 | 57.42 |
| 16.2684 | 5.44863 | 25.67 |
| 16.4624 | 5.38484 | 32.93 |
| 16.8967 | 5.24739 | 90.90 |
| 19.3772 | 4.58091 | 10.50 |
| 22.4767 | 3.95573 | 100.00 |
| 23.4111 | 3.79992 | 20.49 |
| 23.5330 | 3.78051 | 44.02 |
| 23.6735 | 3.75840 | 21.92 |
| 24.0477 | 3.70076 | 13.67 |
| 24.5716 | 3.62303 | 13.43 |
| 25.1240 | 3.54460 | 12.46 |
| 26.6602 | 3.34374 | 19.10 |
| 28.1333 | 3.16930 | 12.07 |
| 28.2443 | 3.15971 | 22.49 | including, the forms whose diffraction angles correspond to within ±0.2°.

6. The agomelatine complex according to claim 1, which is the agomelatine/benzenesulphonic acid (2/1) complex.

7. The agomelatine complex according to claim 6, having the following X-ray powder diffraction diagram expressed in terms of interplanar distance d, Bragg's angle 2 theta (expressed in °±0.2), and relative intensity:

| 2-Theta (°) exp. | d (Å) exp. | Intensity (%) |
|---|---|---|
| 8.0711 | 10.95469 | 35.25 |
| 12.6820 | 6.98026 | 68.37 |
| 12.7706 | 6.93203 | 65.37 |
| 13.0114 | 6.80427 | 15.18 |
| 13.3054 | 6.65458 | 31.84 |
| 14.9475 | 5.92700 | 19.42 |
| 15.1121 | 5.86283 | 70.19 |
| 15.4873 | 5.72160 | 14.16 |
| 16.1644 | 5.48344 | 12.98 |
| 17.2360 | 5.14486 | 21.06 |
| 18.1046 | 4.89993 | 36.33 |
| 18.6255 | 4.76406 | 10.91 |
| 18.8009 | 4.72001 | 33.43 |
| 20.0908 | 4.41978 | 30.26 |
| 20.4742 | 4.33788 | 42.37 |
| 20.6921 | 4.29270 | 56.78 |
| 20.8640 | 4.25771 | 26.42 |
| 21.7142 | 4.09289 | 13.88 |
| 23.3683 | 3.80679 | 15.16 |
| 23.6410 | 3.76349 | 100.00 |
| 24.9314 | 3.57154 | 26.81 |
| 25.6543 | 3.47253 | 10.71 |
| 27.5599 | 3.23660 | 14.00 | including the forms whose diffraction angles correspond to within ±0.2°.

8. A process for obtaining the complex of agomelatine and sulphonic acids according to claim 1, wherein:
the agomelatine and sulphonic acids are mixed in an organic or aqueous hydro-organic solvent in the desired proportions;
the solution obtained is stirred and optionally heated at a temperature not greater than the boiling point of the chosen solvent;
the mixture is cooled, with stirring, and the co-crystal precipitates naturally or precipitates after being taken up in a second solvent;
the precipitate obtained is filtered, off and dried.

9. A process for the preparation of the complex of agomelatine and sulphonic acids according to claim 1, wherein the two constituents are co-ground.

10. A process for the preparation of the complex of agomelatine and sulphonic acids according to claim 1, wherein the two constituents are mixed in an organic or aqueous-organic solvent and are then frozen and dried at very low temperature.

11. A process for the preparation of the complex of agomelatine and sulphonic according to claim 1, wherein the powders of agomelatine and the acid in question are mixed in a mixer and then the mixture is extruded by means of twin-screw extrusion without a die in order to obtain a solid grain directly at the outlet of the extruder.

12. A pharmaceutical composition comprising as active ingredient the complex of agomelatine and sulphonic acids according to claim 1, in combination with one or more inert, non-toxic, pharmaceutically acceptable carriers.

13. A method of treating disorders of the melatoninergic system comprising administering to a subject in need thereof a complex of agomelatine and sulphonic acids according to claim 1, alone or in combination with one or more inert, non-toxic and pharmaceutically acceptable carriers.

14. A method of treating a condition selected from stress, sleep disorders, anxiety disorders, including generalised anxiety disorder, obsessive compulsive disorders, mood disorders, including bipolar disorders, major depression, seasonal affective disorder, insomnia and fatigue due to jet-lag, panic attacks, melancholia, appetite disorders, insomnia, pain, psychotic disorders, epilepsy, diabetes, Parkinson's disease, senile dementia, disorders associated with normal or pathological aging, migraine, conditions requiring an ovulation inhibitor and conditions requiring an immunomodulator in a subject in need thereof, comprising administration of the complex of agomelatine and sulphonic acids according to claim 1, alone or in combination with one or more inert, non-toxic and pharmaceutically acceptable carriers.

* * * * *